(12) United States Patent
Wiklof

(10) Patent No.: US 7,435,217 B2
(45) Date of Patent: Oct. 14, 2008

(54) SCANNED BEAM IMAGERS AND ENDOSCOPES WITH POSITIONABLE LIGHT COLLECTOR

(75) Inventor: Christopher A. Wiklof, Everett, WA (US)

(73) Assignee: Microvision, Inc., Redmond, WA (US)

( * ) Notice: Subject to any disclaimer, the term of this patent is extended or adjusted under 35 U.S.C. 154(b) by 29 days.

(21) Appl. No.: 11/735,922

(22) Filed: Apr. 16, 2007

(65) Prior Publication Data
US 2007/0244365 A1 Oct. 18, 2007

Related U.S. Application Data

(60) Provisional application No. 60/792,990, filed on Apr. 17, 2006.

(51) Int. Cl.
*A61B 1/06* (2006.01)
*A61B 1/04* (2006.01)

(52) U.S. Cl. ............... 600/173; 600/160; 600/109; 600/476

(58) Field of Classification Search ........... 600/160, 600/182, 109, 173, 476–478
See application file for complete search history.

(56) References Cited

U.S. PATENT DOCUMENTS

| | | | | |
|---|---|---|---|---|
| 5,129,897 A | * | 7/1992 | Daikuzono | 606/16 |
| 5,611,017 A | * | 3/1997 | Lee et al. | 385/114 |
| 6,370,422 B1 | * | 4/2002 | Richards-Kortum et al. | 600/478 |
| 6,485,413 B1 | * | 11/2002 | Boppart et al. | 600/160 |
| 6,564,087 B1 | * | 5/2003 | Pitris et al. | 600/478 |
| 6,975,898 B2 | * | 12/2005 | Seibel | 600/473 |
| 2005/0038322 A1 | * | 2/2005 | Banik | 600/129 |
| 2006/0149134 A1 | * | 7/2006 | Soper et al. | 600/182 |

* cited by examiner

*Primary Examiner*—John P Leubecker
(74) *Attorney, Agent, or Firm*—Kevin D. Wills

(57) ABSTRACT

Apparatuses and methods for scanned beam imagers and scanned beam endoscopes having a positionable light collector are disclosed. In one aspect, a scanned beam imager includes a scanned beam source operable to scan a beam across a FOV and a light collector structured to collect light affected by the FOV. The light collector is positionable relative to the beam scanned by the scanned beam source. Scanned beam endoscopes and methods of performing endoscopy are also disclosed that implement the above teachings.

37 Claims, 12 Drawing Sheets

SCANNED BEAM IMAGERS AND ENDOSCOPES WITH POSITIONABLE LIGHT COLLECTOR

CROSS-REFERENCE TO RELATED APPLICATION

This application claims the benefit of U.S. Provisional Application No. 60/792,990, filed Apr. 17, 2006.

The entire disclosure of the prior application is considered to be part of the disclosure of the instant application and is hereby incorporated by reference therein.

TECHNICAL FIELD

This disclosure relates to scanned beam systems and, more particularly, to scanned beam imagers and endoscopes.

BACKGROUND

Video endoscopes have been in general use since the 1980s for viewing the inside of the human body. Endoscopes are typically flexible or rigid devices that have an endoscope tip including an imaging unit, such as a digital camera or a scanned beam imager, configured for collecting light and converting the light to an electronic signal. The electronic signal is sent up a flexible tube to a console for display and viewing by a medical professional such as a doctor or nurse.

To improve performance, specialized endoscopes have been developed to best accomplish their intended function. For example, upper endoscopes are used for examination of the esophagus, stomach and duodenum, colonoscopes are used for examining the colon, angioscopes are used for examining blood vessels, bronchoscopes are used for examining the bronchi, laparoscopes are used for examining the peritoneal cavity, and arthroscopes are used for examining joint spaces. Instruments to examine the rectum and sigmoid colon, known as flexible sigmoidoscopes, have also been developed. The discussion of endoscopes herein generally applies to these and other types of endoscopes, and the term "endoscope" as used herein encompasses all these and other such devices.

Scanned beam endoscopes are a fairly recent innovation, and an example of a scanned beam endoscope is disclosed in U.S. patent application Ser. No. 10/873,540 ("'540 application") entitled SCANNING ENDOSCOPE, hereby incorporated by reference and commonly assigned herewith. FIGS. 1 through 3 show a scanned beam endoscope disclosed in '540 application. As shown in the embodiment of FIG. 1, the scanned beam endoscope 100 includes a controller 102, monitor 104, and optional pump 106, all of which may be mounted on a cart 108, and collectively referred to as console 110. The console 110 communicates with a handpiece 112 through an external cable 114, which is connected to the console 110 via connector 116. The handpiece 112 is operably coupled to the pump 106 and an endoscope tip 120. The handpiece 112 controls the pump 106 in order to selectively pump irrigation fluid through a hose 126 and out of an opening of the endoscope tip 120 in order to lubricate a body cavity that the endoscope tip 120 is disposed within. The endoscope tip 120 includes a scanning tip 118 having a scanning module configured to scan a beam across a field-of-view (FOV).

The endoscope tip 120 and scanning tip 118 thereof are configured for insertion into a body cavity for imaging internal surfaces thereof. In operation, the scanning tip 118 scans a beam of light over a FOV, collects the reflected light from the interior of the body cavity, and sends a signal representative of an image of the internal surfaces to the console 110 for viewing and use by the medical professional.

FIGS. 2 and 3 depict the scanning tip 118 and a scanning module 127 of the scanning tip 118, respectively. Referring to FIG. 2, the scanning tip 118 includes a housing 130 that encloses and carries the scanning module 127, a plurality of detection optical fibers 132, and an end cap 131 affixed to the end of the housing 130. The detection optical fibers 132 may be disposed peripherally about the scanning module 127 within the housing 130. Referring to FIG. 3, the scanning module 127 has a housing 134 that encloses and supports a micro-electro-mechanical (MEMS) scanner 136 and associated components, an illumination optical fiber 138 affixed to the housing 134 by a ferrule 142, and a beam shaping optical element 140. A dome 133 is affixed to the end of the housing 130 and may be hermetically sealed thereto in order to protect the sensitive components of the scanning module 127.

In operation, the scanning tip 118 is inserted into a body cavity. The illumination optical fiber 138 outputs a beam 144 that is shaped by the beam shaping optical element 140 to form a shaped beam 146 having a selected beam shape. The shaped beam 146 is transmitted through an aperture in the center of the MEMS scanner 136, reflected off a first reflecting surface 148 of the interior of the dome to the front of the scanner 136, and then reflected off of the scanner 136 as a scanned beam 150 through the dome 133. The scanned beam 150 is scanned across a FOV and reflected off of the interior of a body cavity. At least a portion of the reflected light from the FOV (e.g., specular reflected light and diffuse reflected light also referred to as scattered light) is collected by the detection optical fibers 132. Accordingly, the reflected light collected by the detection optical fibers 132 may be converted to an electrical signal using optical-electrical converters, such as photodiodes, and the signal representative of an image may be sent to the controller 102 for image processing and the image displayed on the monitor 104. While the scanned beam endoscope 100 is an effective endoscope, the scanning tip 118 has a diameter that may be larger than desired for some applications due to the detection optical fibers 132 being positioned peripherally about the scanning module 127.

SUMMARY

Apparatuses and methods for scanned beam imagers and scanned beam endoscopes having a positionable light collector are disclosed. In one aspect, a scanned beam imager is disclosed. The scanned beam imager includes a scanned beam source operable to scan a beam across a FOV and a light collector structured to collect light affected by the FOV. The light collector is positionable relative to the scanned beam source.

In another aspect, a method of capturing an image of a FOV is disclosed. In the method, a beam is scanned across the FOV. A light collector is positioned relative to the beam. At least a portion of light affected by the FOV is collected with the light collector. The image, which is characteristic of the FOV, is generated based upon the affected light collected by the light collector.

In another aspect, a scanned beam endoscope is disclosed. The scanned beam endoscope includes a scanning tip operable to scan a beam across a FOV and a light collector structured to collect light affected by the FOV. The light collector is positionable relative to the scanning tip.

In yet another aspect, a method of performing endoscopy is disclosed. In the method, a scanning tip of an endoscope tip is introduced into a body cavity. A beam emitted from the scanning tip is scanned across a FOV within the body cavity. A light collector may be positioned relative to the scanning tip. At least a portion of light affected by the FOV is collected with the light collector.

DETAILED DESCRIPTION OF THE EMBODIMENTS

Figure 1:
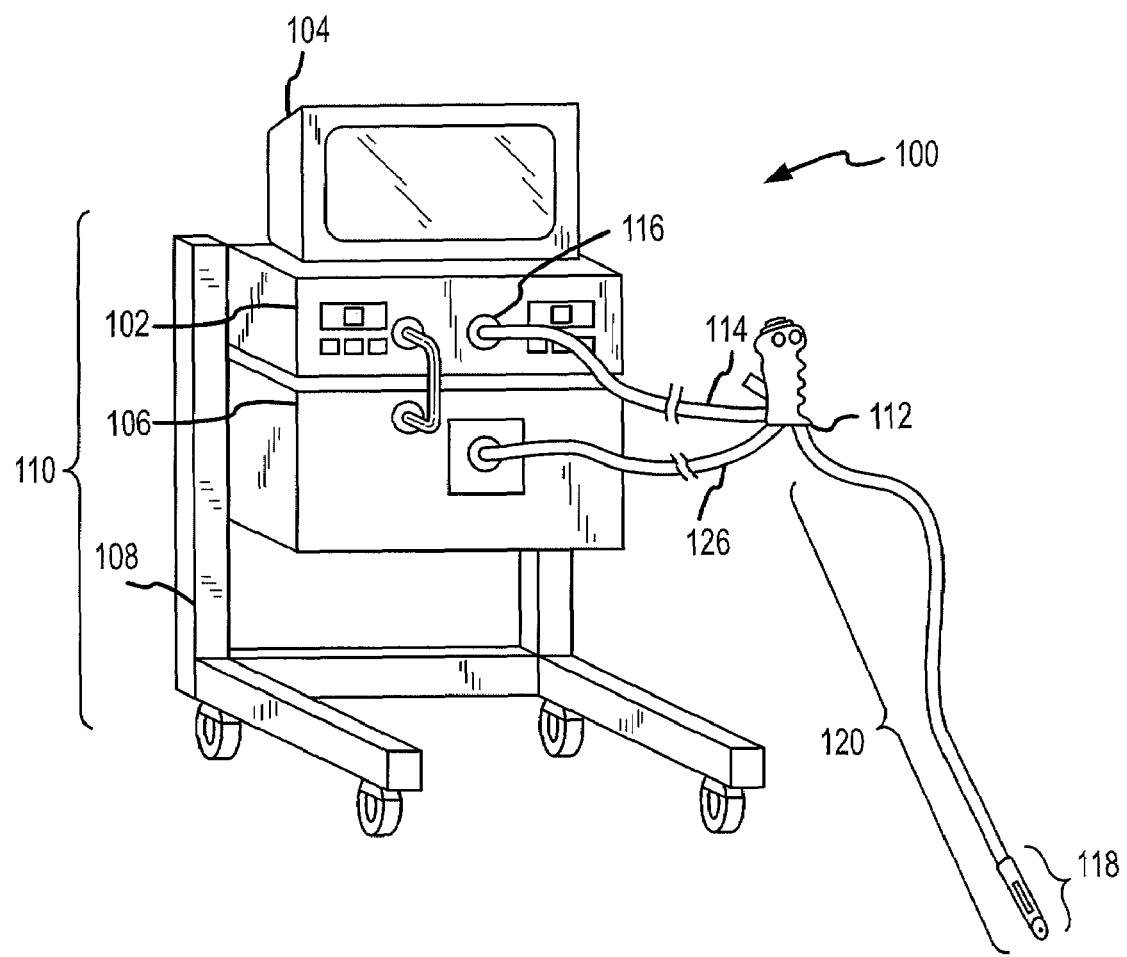
FIG. 1 is schematic illustration of a scanned beam endoscope according to the prior art.

Apparatuses and methods for scanned beam imagers and scanned beam endoscopes having a positionable light collector are disclosed. Many specific details of certain embodiments are set forth in the following description and in the figures in order to provide a thorough understanding of such embodiments. One skilled in the art, however, will understand that there may be additional embodiments, or that the disclosed embodiments may be practiced without several of the details described in the following description. In the figures and description that follow, like elements and features are identified by like or similar reference numerals.

Figure 4:
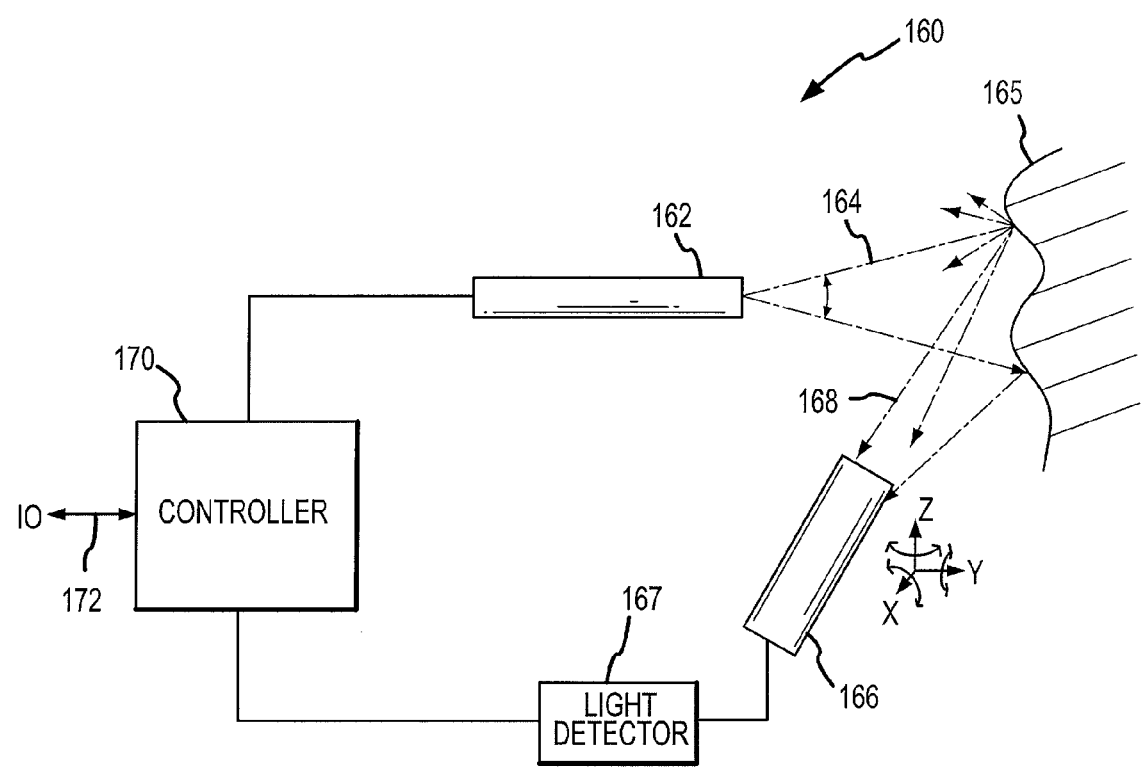
FIG. 4 is a schematic illustration of a scanned beam imager in which the light collector thereof can be positioned relative to the scanned beam source in accordance with one embodiment.

FIG. 4 is a schematic diagram of a scanned beam imager 160 in accordance with one embodiment. The scanned beam imager 160 includes a scanned beam source 162 operable to scan a beam 164 across a FOV onto an area of interest of an object 165. The scanned beam imager 160 further includes a light collector 166 that is positionable relative to the scanned beam source 162 and the beam 164 emitted therefrom. The light collector 166 is a separate structure from the scanned beam source 162 and, thus, can be positioned independent of the position of the scanned beam source 162. The light collector 166 is configured for collecting light affected by the area of interest on the object 165. A light detector 167, such as one or more photodiodes, is optically coupled to the light collector 166 so that the affected light collected by the light collector 166 may be received by the light detector 167 and converted to electrical signals. While the beam 164 illuminates the spots on the object 165, a portion of the illuminating beam 164 is reflected (e.g., specular reflected light and diffuse reflected light also referred to as scattered light), absorbed, refracted, transmitted, or otherwise affected according to the properties of the object or material at the spots to produce affected light. The affected light is shown in FIG. 4 as reflected light 168 reflected by the object 165 and collected by the light collector 166. The light collector 166 may be lenses or another structure at least partially transparent to the reflected light 168. Accordingly, the scanned beam imager 160 enables the user to position the light collector 166 to a desired position and orientation relative to the scanned beam source 162 and the object 165.

A controller 170 is coupled to the scanned beam source 162 and the light detector 166. The controller 170 controls the scanning of the beam 164 of the scanned beam source 162. The light detector 167 generates electrical signals corresponding to the amount of the affected light 168 received by the light collector 166. The electrical signals drive the controller 170, which generates a digital representation of the area of interest and transmits it for further processing, decoding, archiving, printing, display, or other treatment or use via interface 172. The image of the FOV may be generated by correlating the time at which particular pixels in the FOV are scanned with the beam 164 or the time at which the reflected light 168 is received by the light detector 167 to the position of the pixels in the particular scan pattern being used. In another embodiment, the conversion of the optical signals associated with the reflected light 168 may be converted to electrical signals at the controller 170.

Figure 5:
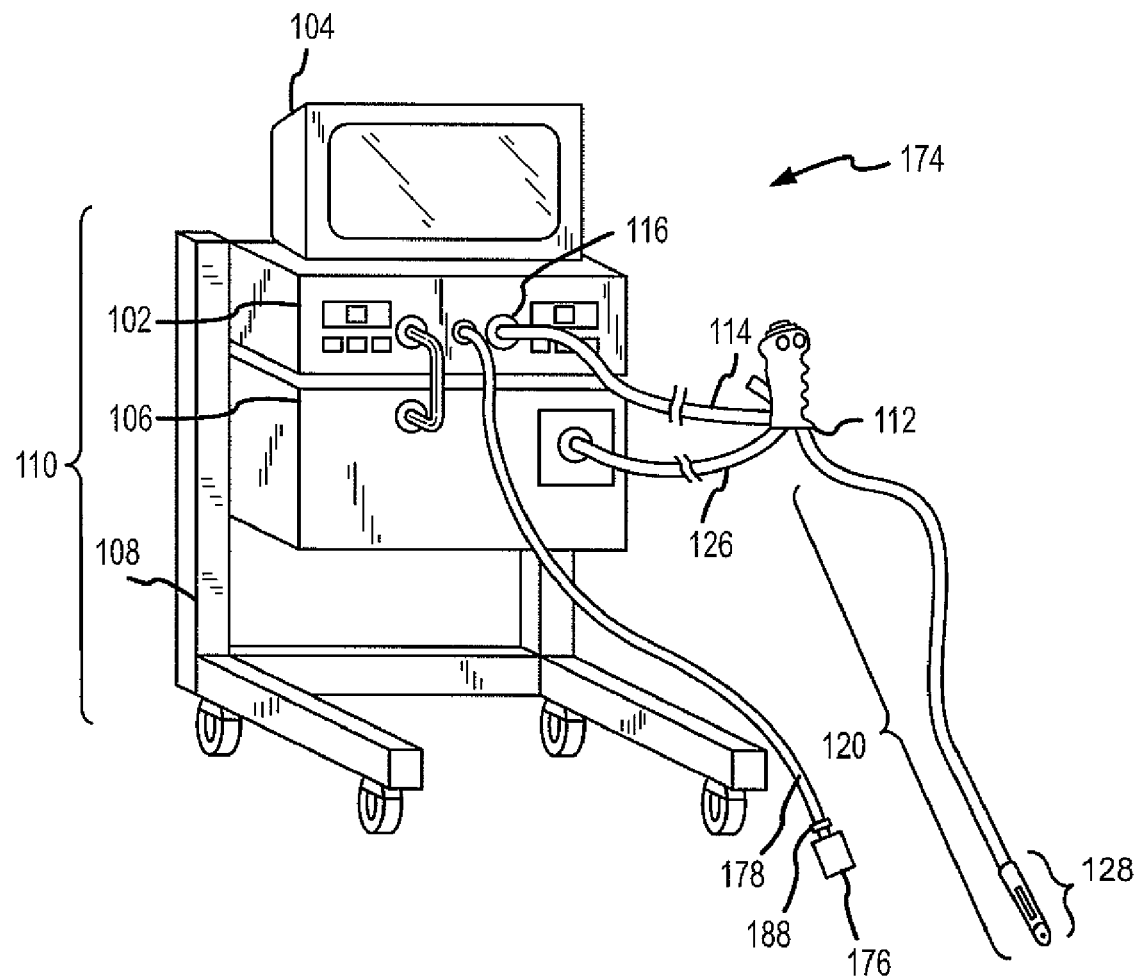
FIG. 5 is a schematic illustration of a scanned beam endoscope incorporating the teachings of the scanned beam imager of FIG. 4 in accordance with one embodiment.

The teachings of the scanned beam imager 160 may be implemented in a scanned beam endoscope. FIG. 5 is a schematic illustration of a scanned beam endoscope 174 in accordance with one embodiment that incorporates such teachings. The scanned beam endoscope 174 has many of the same components of the scanned beam endoscope 100 shown in FIG. 1. Therefore, in the interest of brevity, components in both scanned beam endoscopes 100 and 174 that are identical to each other have been provided with the same reference numerals, and an explanation of their structure and function will not be repeated unless the components function differently in the two scanned beam endoscopes 100 and 174.

Figure 2:
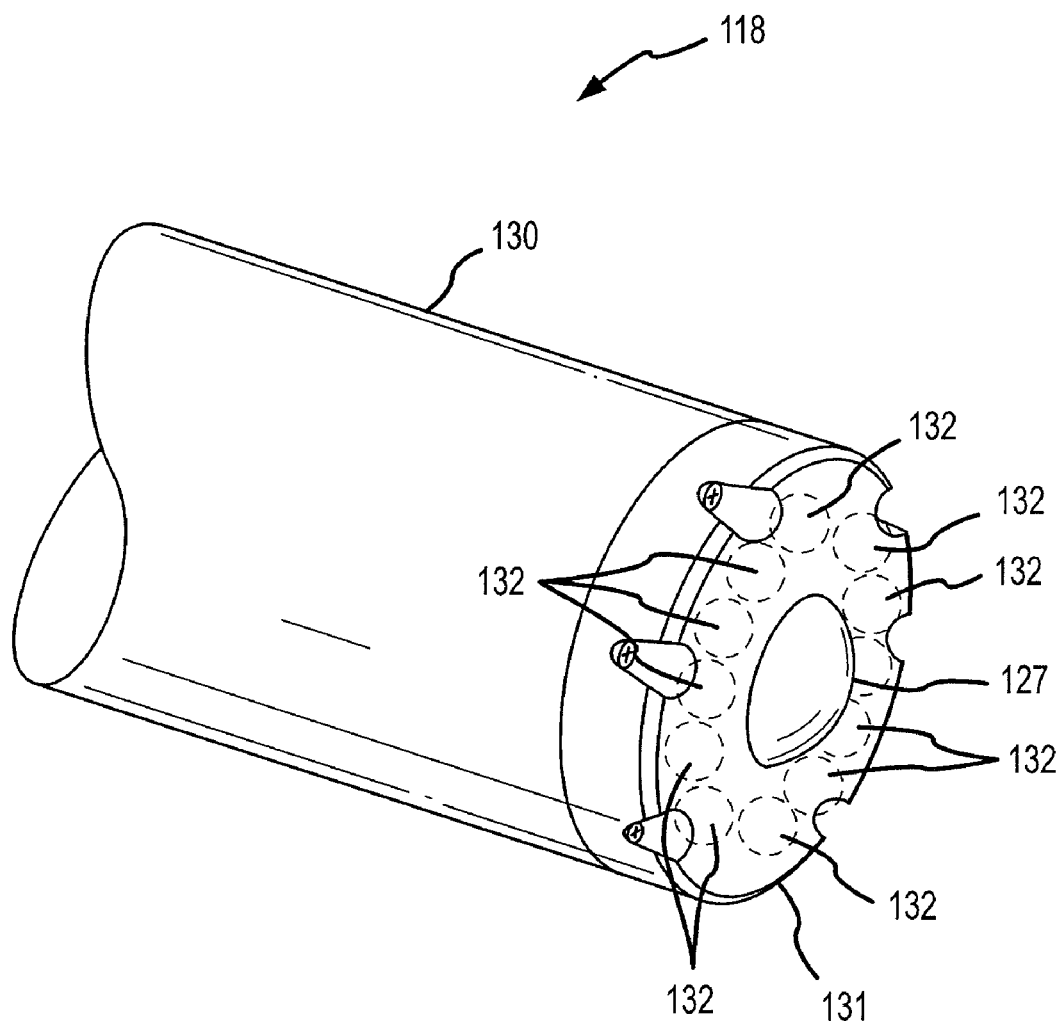
FIG. 2 is a schematic partial isometric view of a scanning tip shown in FIG. 1 according to the prior art.
Figure 3:
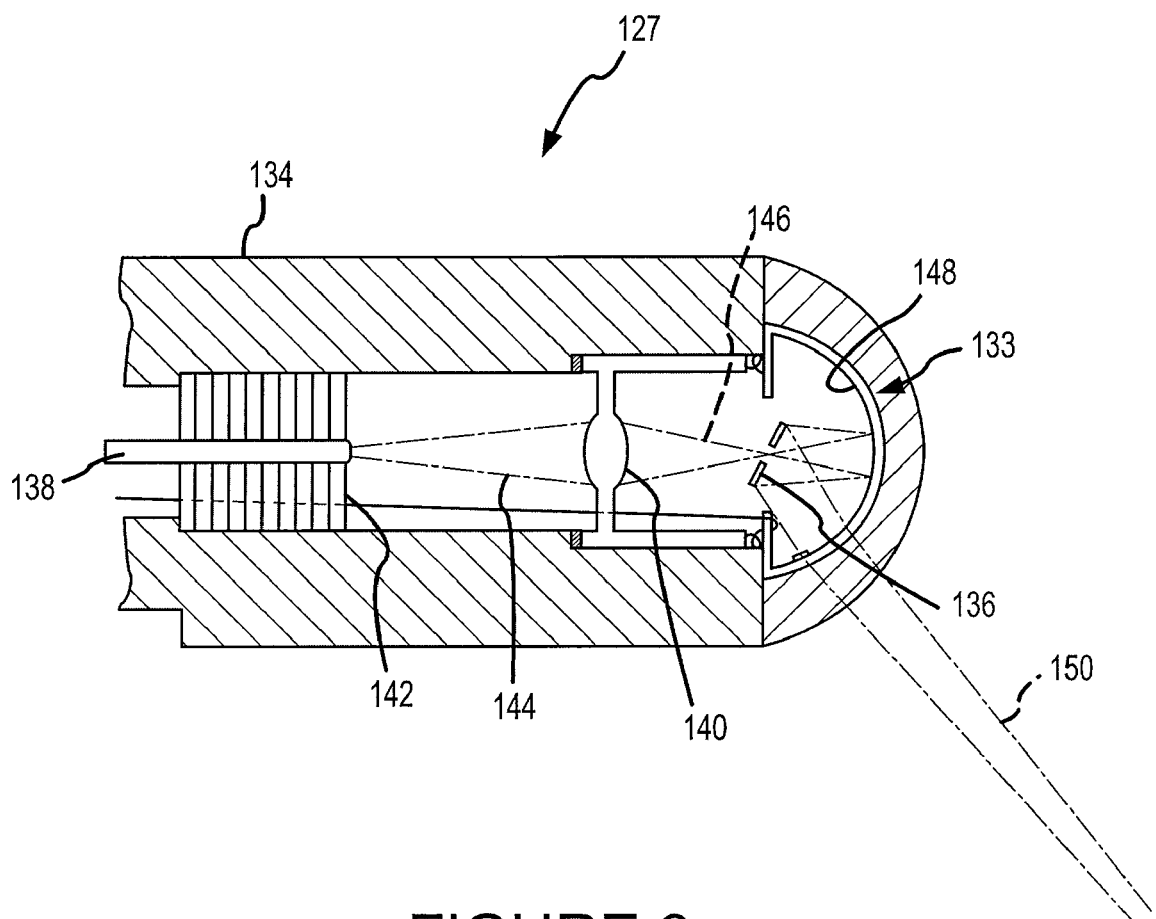
FIG. 3 is a schematic partial side cross-sectional view of the scanning module of FIG. 2 according to the prior art.

The scanned beam endoscope 174 includes a light collector 176 optically coupled to a light detector 188. The scanning tip 128 includes a scanned beam source that, in one embodiment, is configured as a discretely packaged version of the scanning module 127 shown in FIGS. 2 and 3. The scanning module 127 is a component of the endoscope tip 120 and the scanning module 127 may form all or part of the scanning tip 128. The light detector 188 may be coupled to the controller 102 via a cable 178. The light detector 188 may be one or more photodiodes for converting the affected light received from the object being imaged to electrical signals and may be attached or otherwise coupled to the light collector 176. The cable 178 may include electrical wires that transmit the electrical signals to the controller 102. In another embodiment, the cable 178 may include one or more optical fibers that transmit optical signals associated with affected light provided by the FOV and received by the light collector 176 to the controller 102, which then converts the optical signals to electrical signals and generates an image for display on the monitor 104. In such an embodiment, the light detector 188 may be located in the console 110 and coupled to the controller 102.

As with the scanned beam imager 160 of FIG. 4, the scanned beam endoscope 174 enables the user to position the light collector 176 within or proximate a body cavity relative to the scanning tip 128. Additionally, since light collection function is not performed by detection optical fibers or light detectors that are included in the scanning tip 128, the scanning tip 128 may have a smaller diameter, which facilitates endoscopic examination because incisions can be made smaller and patient discomfort may be reduced if the scanning tip 128 is inserted into a preexisting body opening. In some embodiments, the diameter of the scanning tip 128 may be reduced by a factor of four to sixteen compared to the conventional scanning tip 118 shown in FIGS. 1 and 2. Alternatively, additional scanning tip real estate may be allocated to other functionality including, but not limited to, a working channel, a lens cleaning apparatus, or other specialized instruments.

Figure 6A:
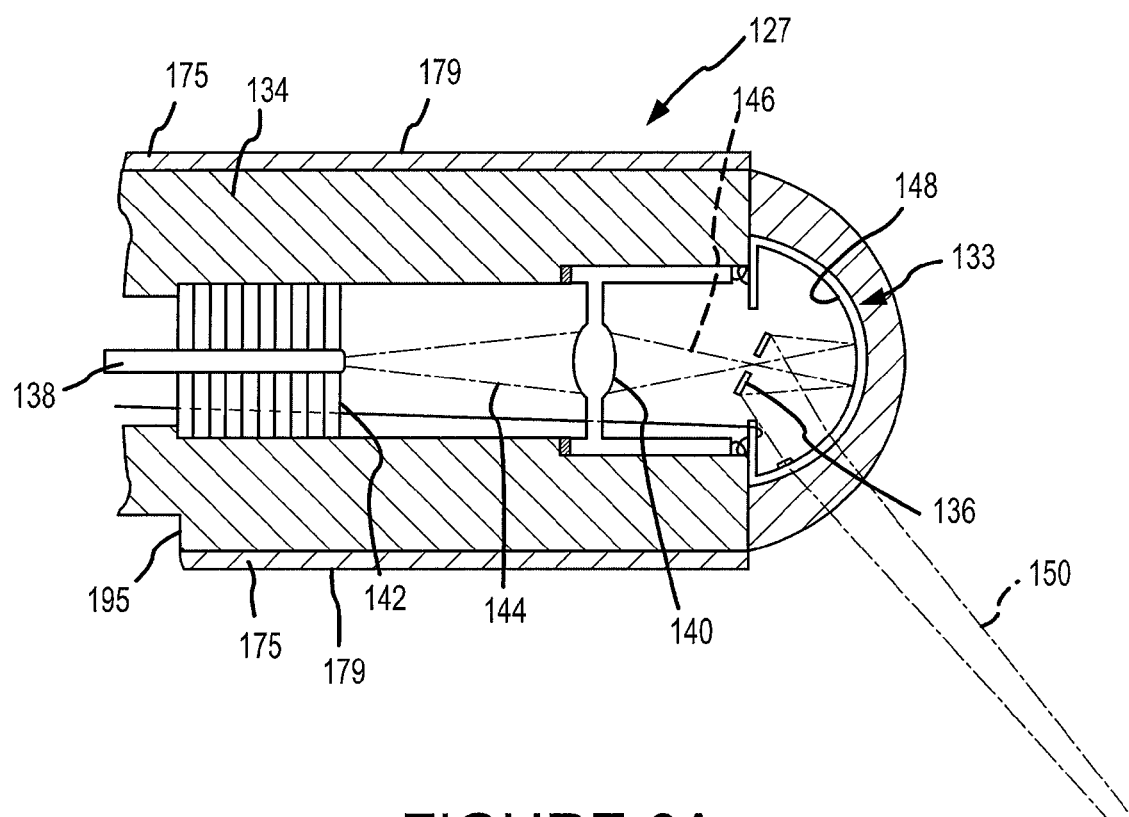
FIG. 6A is a schematic partial side cross-sectional view of a scanning module that may be used in the scanned beam endoscope of FIG. 5.

In one embodiment for the scanning module 127 shown in FIG. 6A, an outer sheath 175 is provided. The outer sheath 175 may be affixed to the housing 134 and disposed circumferentially about the housing 134 to provide an outer surface 179 to protect cross-contamination between the inner surfaces of the scanning module 127 and the body cavity of the patient, provide a surface that seals with a trocar, facilitate handling, among various other types of functionality. A registration notch 195 may be formed in the housing 134 to aid in registering scanning module 127 with the scanning tip 118. In another embodiment, the outer sheath 175 may be disposed only about the portion of the housing 134 in which the registration notch 195 is formed in and regions adjacent thereto.

Figure 6B:
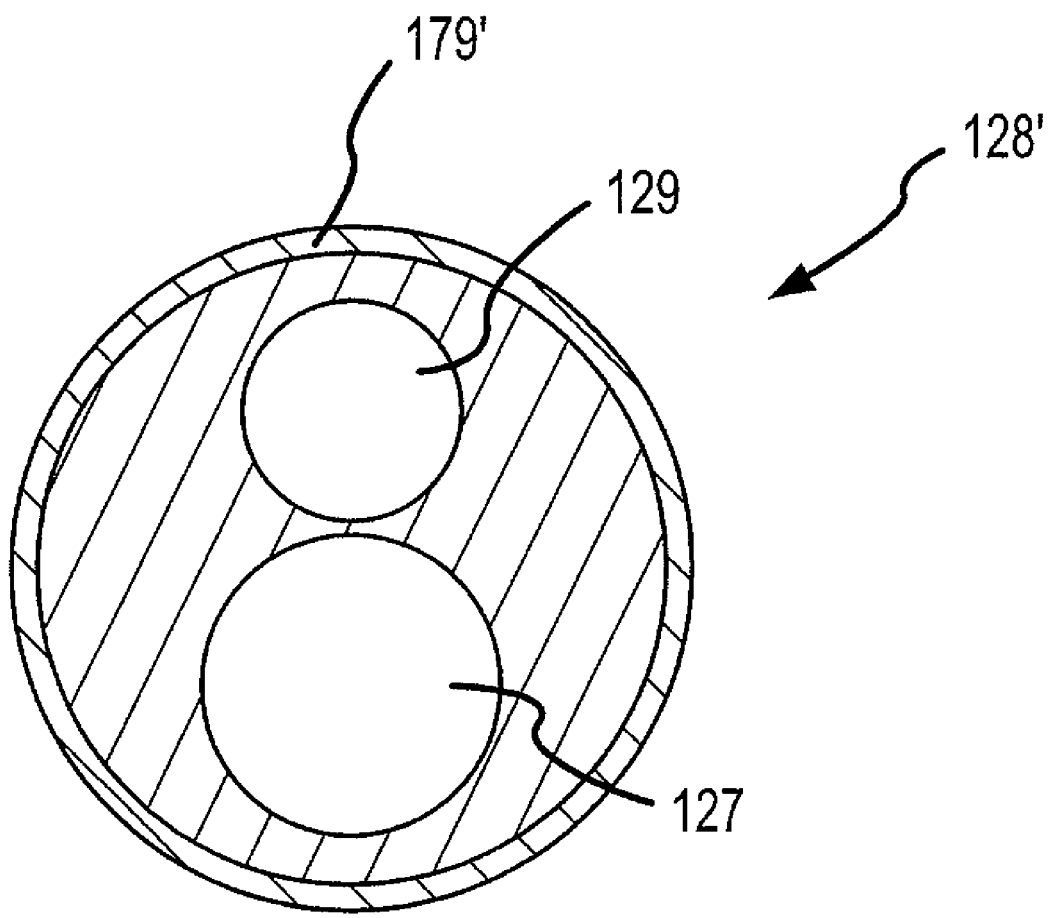
FIG. 6B is a schematic front cross-sectional view of a scanning tip including a scanning module and a working channel through which the light collector shown in FIG. 5 may be inserted in accordance with one embodiment.

According to other embodiments, the scanning tip 128 may include light collection fibers and/or light detectors to provide additional light collection and/or light detection capabilities that may be introduced using a separate light collector 176. For example, it may be desirable that the scanning tip 128 is configured as the scanning tip 118 shown in FIGS. 1-3 with its own light collection capabilities through use of the detection optical fibers 132 or light detection elements positioned about the scanning module 127, such as photo detectors. Such an approach may be useful, for example, when longer range or higher signal-to-noise imaging is desired. The integral light collection and/or light detection capabilities of the scanning tip 128 may be used for a portion of a procedure. When the practitioner desires additional capabilities offered by more or separate light collection, such light collection may be introduced to the imaging volume as an auxiliary light collector, for example through a separate trocar or through a working channel of the endoscope tip 120. When the practitioner no longer needs the additional capabilities of the additional light collection, the auxiliary light collector may be withdrawn and the procedure may continue using the integral light collection and/or detection. FIG. 6B shows one embodiment of the scanning tip 128' that includes the scanning module 127 and one or more working channels 129 in the scanning tip 128' and generally surrounded by an outer, protective sheath 179'. The light collector 176 may be inserted through the working channel 129 and into a body cavity for implementation of the above described endoscopic procedures. The working channel 129 may also be used for insertion of surgical tools, diagnostic tools, fluids such as air for inflation, saline for irrigation, or in vivo fluids for removal and disposal into a body cavity.

Figure 7A:
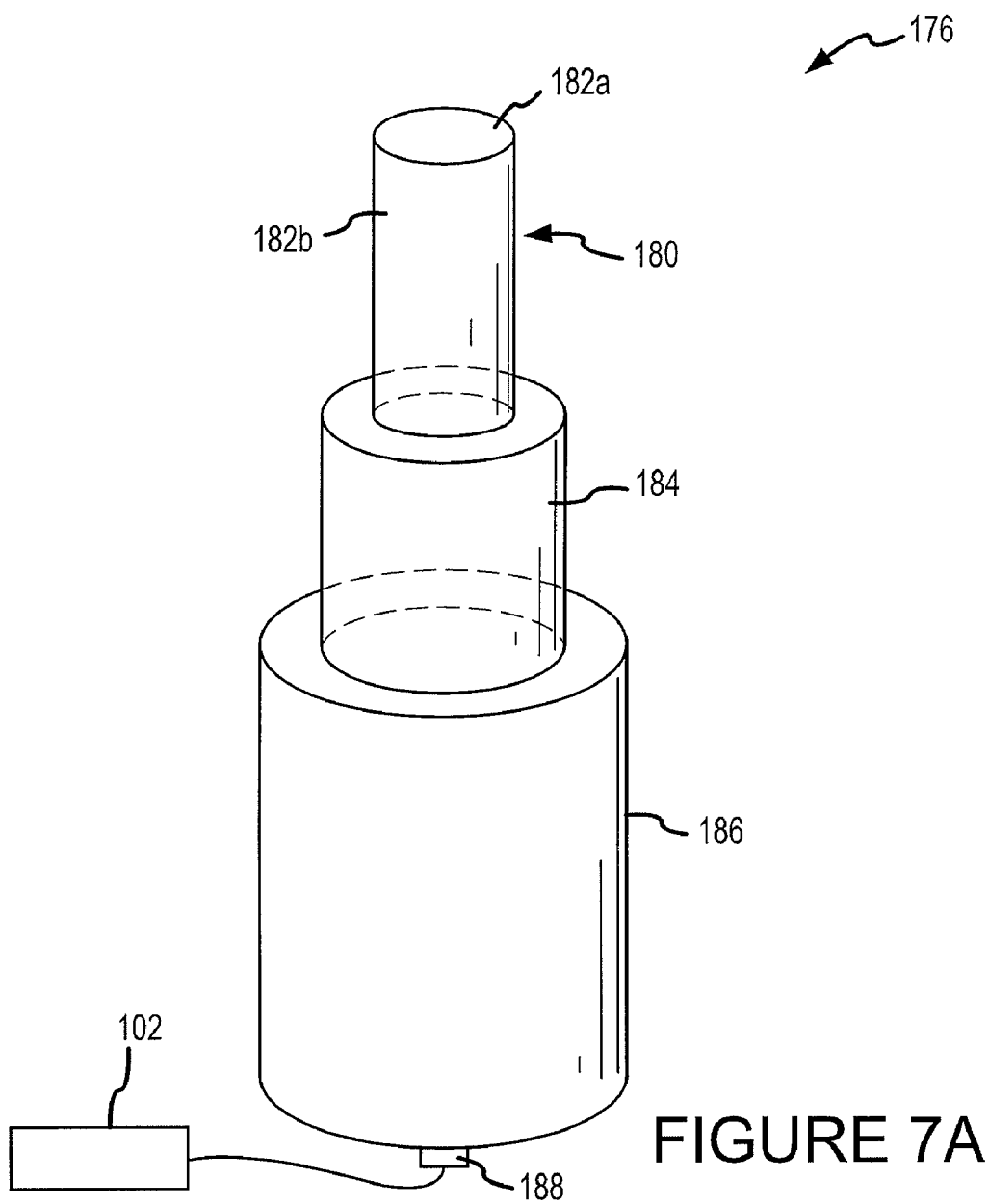
FIG. 7A is a schematic isometric view of one embodiment of a light collector and associated light detector suitable for use with the scanned beam imager of FIG. 4 and the scanned beam endoscope of FIG. 5.
Figure 7B:
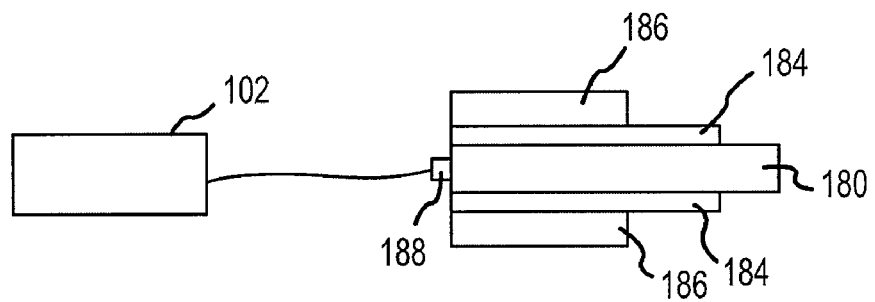
FIG. 7B is a schematic sectional view of FIG. 7A.

FIGS. 7A and 7B show schematic views of one embodiment for the light collector 176 shown in FIG. 5 and may also be used for the light collector 166 of FIG. 4. The light collector 176 includes a light transmission portion 180 including collection surfaces 182a-b. The light transmission portion 180 is formed from a material at least partially transparent to the affected light provided by the FOV. Suitable materials for forming the light transmission portion 180 include, but are not limited to, glasses, ceramics, polymeric materials, or another material having suitable optical properties.

A cladding 184 may enclose a portion of the light transmission portion 180 to leave the collection surfaces 182a-b exposed. The cladding 184 may be formed from a material having an index of refraction less that the index of refraction of the light transmission portion 180 so that the cladding 184 functions as a light guiding layer. The cladding 184 may be formed from various reflective materials, such as aluminum, gold, silver, or another suitable reflector that may be plated or sputtered over the light transmission portion 180. A cladding 186 may also partially or completely enclose the cladding 184 to prevent extraneous light from entering the light transmission portion 180. The cladding 186 may be formed from a material, such as a ceramic, glass, or metallic material that is opaque to the wavelengths of the affected light provided by the FOV. If the cladding 184 is opaque to the wavelengths of the affected light from the object being imaged, the cladding 186 may be formed of a material that is not opaque and helps protect the cladding 184 and light transmission portion 180 from environmental or handling damage. A light detector 188, such one or more photodiodes, may be mounted to the end of the light transmission portion 180 opposite the collection surface 182a so that it receives the affected light that propagates through the light transmission portion 180. In some embodiments, the collection surfaces 182 may have a material, such as polyterefluoroethylene (PTFE), tailored to increase the acceptance angle disposed thereon or the collection surfaces 182 may be roughened to increase the acceptance angle. By employing the light collector 176, the detection optical fibers 132 can advantageously be eliminated from the scanning tip 128 to reduce the diameter thereof. In another embodiment, the light collector 176 is an optical fiber or a bundle of optical fibers that collects affected light from the FOV through its end and transmits optical signals to the light detector 188, which may be located in the console 110 of the scanned beam endoscope 174.

During use, a beam is scanned across a FOV using a scanned beam source of the scanning tip 128 and impinges on an area of interest of an object. The light affected by the object in the FOV is collected by at least some of the collection surfaces 182 of the light transmission portion 180 and transmitted to the light detector 188. The light detector 188 converts the optical signals to electrical signals that are further processed by the controller 102 to generate an image characteristic of the FOV that is displayed on the monitor 104 or another output device for further processing, decoding, archiving, printing, display, or other treatment.

In another embodiment, instead of using the light collector 176 to collect affected light and transmit it to the light detectors 188, the light transmission portion 182 and associated claddings 184 and 186 may be eliminated or one or more light detectors 188 may be arrayed on the collection surface 182a and/or 182b. In this embodiment, one or more of the light detectors 188, which may be PIN photodiodes, are arrayed and employed to collect the affected light. As such, the light detectors 188 function not only as light collectors to collect the affected light, but also convert the collected light to an electrical signal locally that may then be transmitted to an external location such as a console 110 of the scanned beam endoscope 174. In embodiments that use local light detection, it may be advantageous to position one or more amplification stages near the light detectors 188, and transmit an amplified signal externally. According to some embodiments, it may be advantageous to position analog-to-digital converters locally and transmit a digital representation of the received light to an external (proximal) location.

Figure 8:
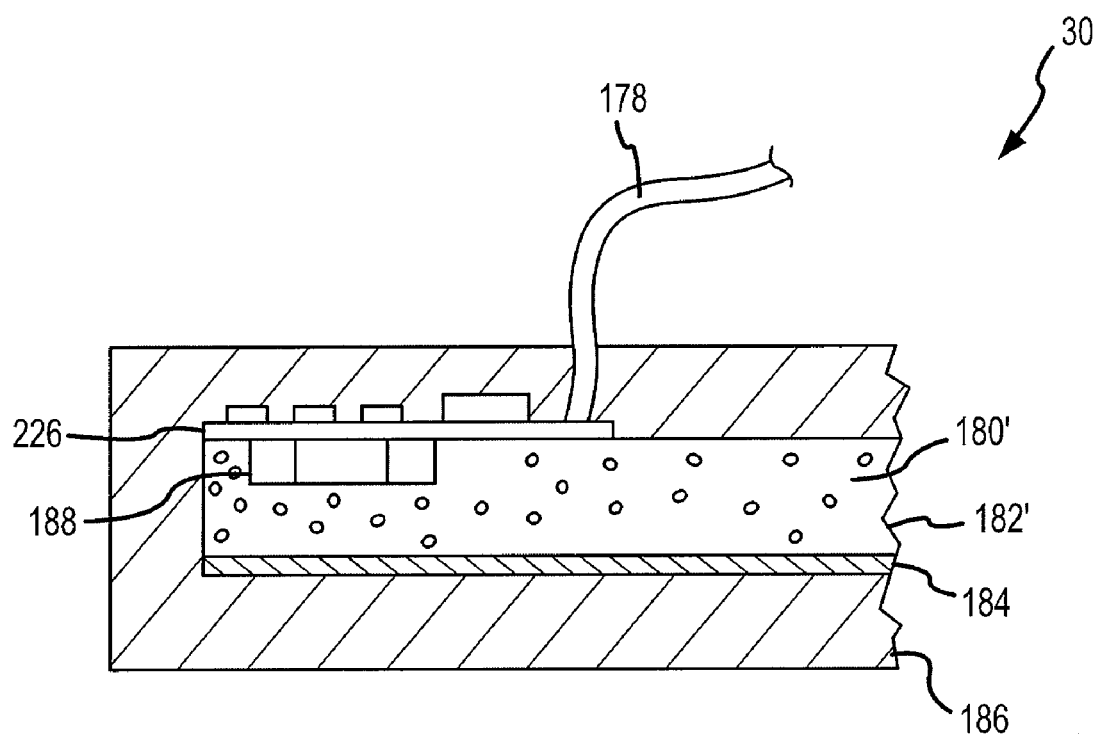
FIG. 8 is a schematic cross-sectional view of a light collector that includes an integrated light detector and amplification electronics in accordance with one embodiment.

FIG. 8 shows one embodiment of a light collector 230 in which the light detector 188, and amplification electronics are integrated into a single structure. The light collector 230 includes a light detector 188 and associated amplification electronics 226 that are disposed within or on the light collector 230. As shown, the light detector 188 may be positioned on one side of a light transmission portion 180' and a cladding 184' positioned on the opposing side of the light transmission portion 180'. Amplification electronics 226, depicted as a printed circuit board, is coupled to the light detector 188 and configured to amplify the received signals from the light detector 188, which are then transmitted via the cable 178 to the controller 102. A cladding 186' partially encloses the cladding 184', the light transmission portion 180', the amplification electronics 226 and leaves a portion 182' of the light transmission portion 180' exposed for collecting affected light from the FOV.

In operation, affected light received from the FOV is collected by the light transmission portion 180' in the same manner as the light collector 176 shown in FIGS. 7A-7B. However, the collected light propagates through the light transmission portion 180' and is received by the integrated light detector 188. The light detector 188 converts the collected optical signals to electrical signals that are further amplified by the amplification electronics 226. The amplified signals are transmitted to the controller 102 via the cable 178. Thus, in the light collector 230, the optical signals are not only converted to electrical signals at the light collector 230, but the electrical signals are amplified prior to transmission to the controller 102 for signal processing.

The amplification electronics 226 may include a first stage amplifier such as a trans-impedance amplifier (TIA) to provide an amplified signal for transmission to the controller 102 of the scanned beam endoscope 174. In another embodiment, two or more stages of amplification may be effected by a TIA and AC-coupled voltage amplifier to provide even greater signal amplification. In yet another embodiment, an analog-to-digital (ADC) may provide a digitized signal for transmission to the controller 102 of the scanned beam endoscope 174. In such an embodiment, a TIA first stage and AC-coupled voltage amplifier second stage may be used to improve signal-to-noise and reduce interference compared to analog transmission.

Figure 9:
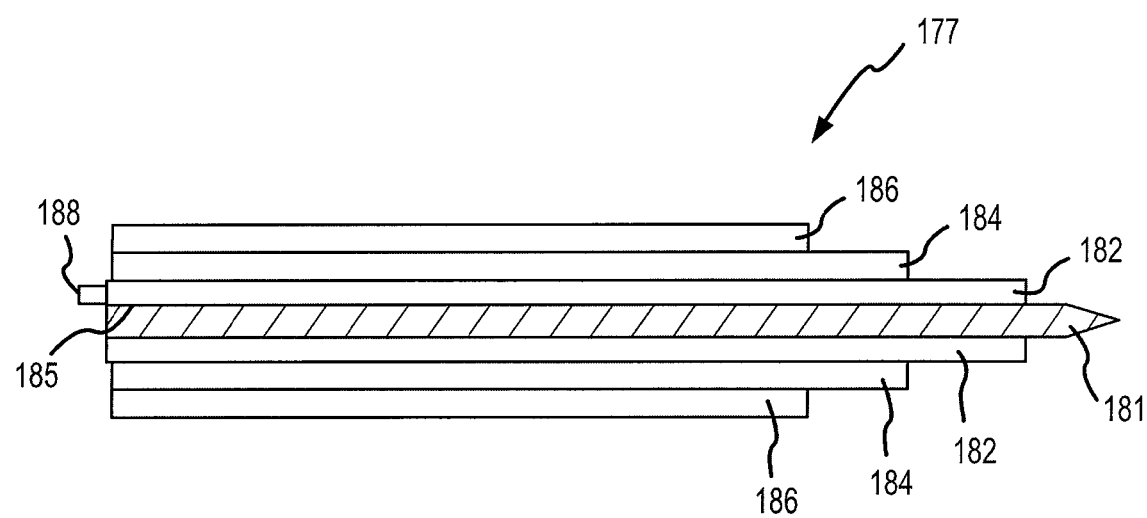
FIG. 9 is a schematic cross-sectional view of a combination light collector/surgical tool in accordance with one embodiment.

The embodiment for the light collector 176 shown in FIGS. 7A-7B is suitable only for collecting light from the FOV. FIG. 9 shows a schematic view of a versatile light collector/surgical tool 177 having a surgical tool 181, such as scalpel or forceps. The light collector/surgical tool 177 includes the light transmission portion 182 formed on and about the surgical tool 181, and the cladding 186 is formed on and about the cladding 184. As with the embodiment shown in FIGS. 7A-7B, affected light from the FOV is collected by the light transmission portion 182 and transmitted therethrough to a light detector 188 that may be mounted to the light collector 177. Accordingly, the light collector 177 is suitable for minimally invasive surgical procedures because only one incision needs to be made for providing a light collection device for image generation purposes and a surgical tool. In the embodiment shown in FIG. 9, the light transmission portion 182 may be formed with a passageway 185 extending therethrough and the surgical tool 181 may be inserted through the passageway and retained on the light transmission portion 182 due to an interference fit or another suitable retention means. In another embodiment, the light transmission portion 182 and the surgical tool 181 may be integrally formed from the same material that the light transmission portion 182 is formed of. Thus, in such an embodiment, the light transmission portion 182 is shaped to define the surgical tool 181.

Figure 10:
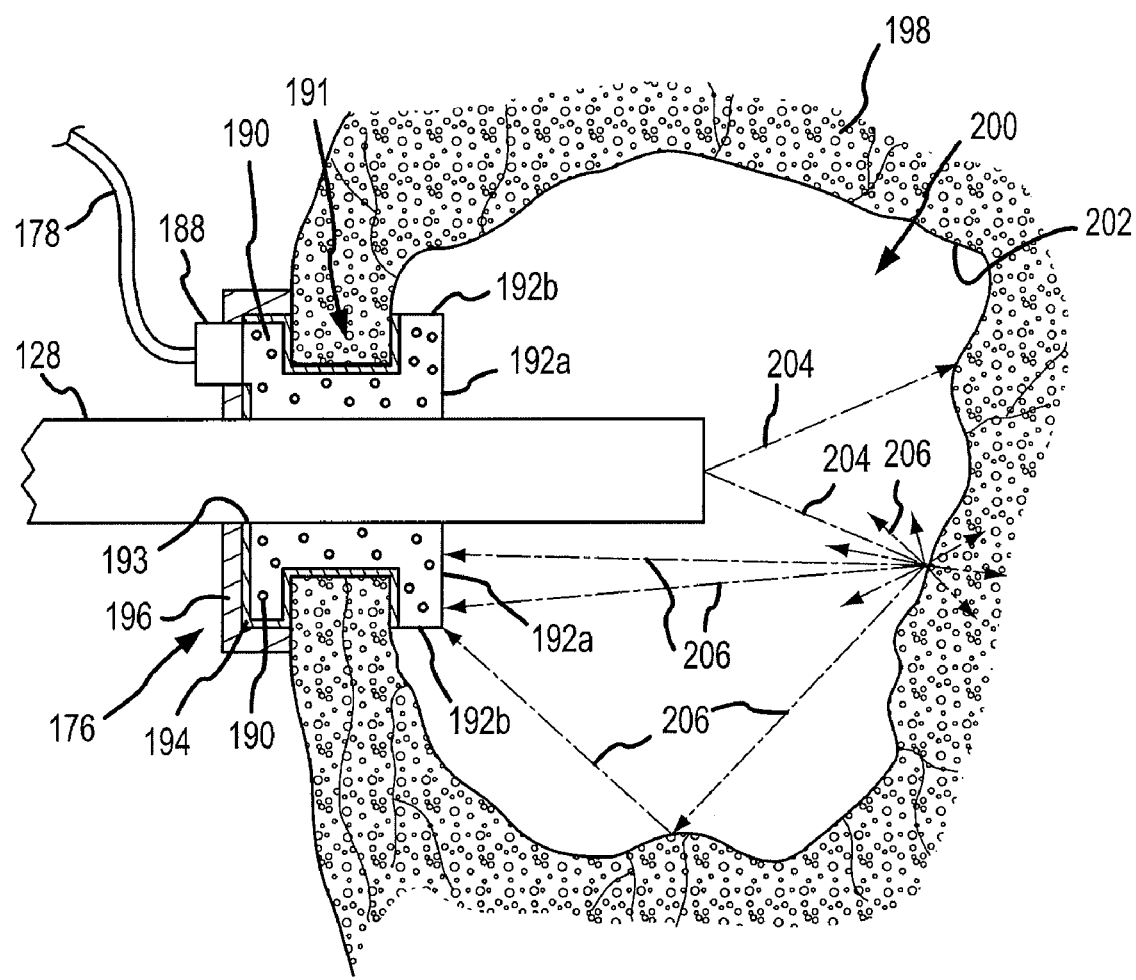
FIG. 10 is a schematic sectional view of a light collector that forms part of a trocar housing for use in endoscopic applications in accordance with one embodiment.

FIG. 10 shows a schematic illustration of an endoscopic application in which the light collector 176 forms at least part of a trocar in accordance with one embodiment. As known in the art, a trocar, typically, includes a trocar housing, a cannula assembly attached to the trocar housing and having a bore therein, and an obturator that slides through the bore to make an incision in a subject. The light collector 176 includes a light transmission portion 190 configured in the general shape of a trocar housing having a bore 193 extending therethrough. The light transmission portion 190 has a generally annular shape with a circumferentially formed recess 191 configured to seal against the skin or other tissue 198 of a subject. The light detector 188 is mounted on the light transmission portion 190 in order to receive affected light from the FOV that propagates through the light transmission portion 190. The light transmission portion 190 further includes collection surfaces 192*a-b* that collects affected light from the FOV. The light collector 176 may also include a cladding 194 covering selected portions of the exterior surface of the light transmission portion 190 to leave the collection surface 192 exposed. A cladding 196 may also cover portions of the light collector 176 and the cladding 194 thereof that will be exposed to ambient light during use. The cladding 196 prevents ambient light from being received by the light detector 188 during use. The light transmission portion 190 and claddings 194 and 196 may be formed from the same materials as discussed above with respect to FIGS. 7A-7B. Although not shown, a cannula assembly may be attached to the trocar housing and all of or part of the cannula assembly may be formed as the light collector in addition to or instead of the trocar housing being employed as the light collector 176.

In use, an incision may be made in the tissue 198 of the subject, using an obturator, for example (not shown), to gain access to a body cavity 200 having an interior surface 202. The light collector 176 is inserted through the incision and the fit is tight enough to establish a seal between the tissue 198 and the cladding 194 of the light collector 176, with the recess 191 receiving a portion of the skin or other tissue 198 of the subject. The scanning tip 128 is inserted through the bore 193 in the light collector 176 and into the body cavity 200. The body cavity 200 may be sufflated using a conventional means such as using provisions included in the light transmission portion 190 for providing positive gas pressure to the inside of the body cavity 200 to increase the volume thereof. Although not shown, such means may include a port formed in the light transmission portion 190 and an associated valve assembly connected to a gas source that enables controlling fluid flow into the body cavity 200. The scanning tip 128 scans a beam 204 across a FOV to impinge on the interior surface 202 of the body cavity 200. The beam 204 is reflected as reflected light 206, which may be diffuse or specular reflected light. At least a portion of the reflected light 206 is received by the collection surfaces 192*a-b* of the light transmission portion 190. The reflected light 206 propagates through the light transmission portion 190 to the light detector 188. As previously discussed, at the light detector 188, the reflected light 206 is converted to electrical signals that are transmitted via the cable 178 to the controller 102, which generates an image of the interior surfaces 202 of the body cavity 200.

Figure 11:
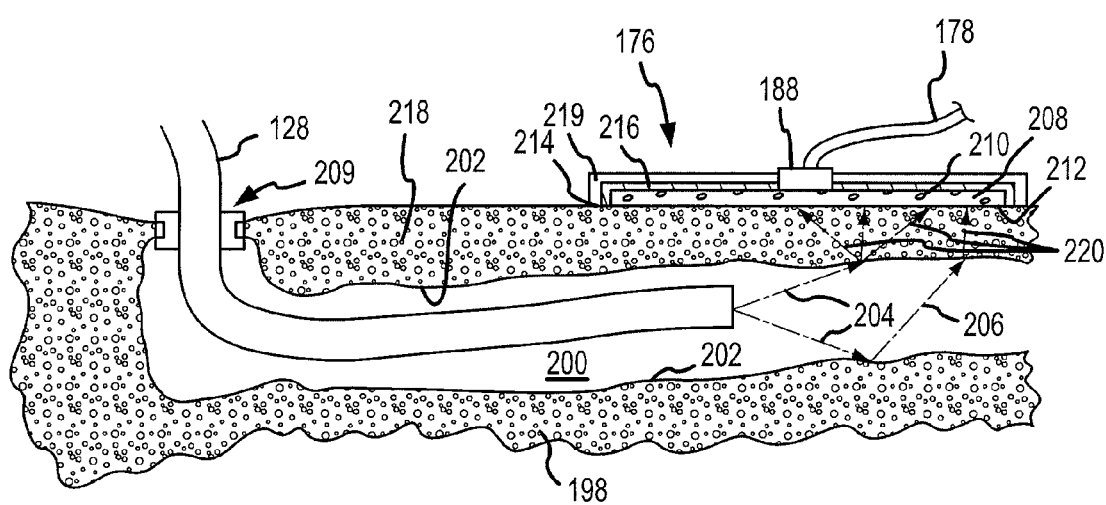
FIG. 11 is a schematic sectional view of a light collector used to detect affected light transmitted through a region of interest of a subject in accordance with one embodiment.

FIG. 11 shows a schematic illustration of another embodiment for the light collector 176 suitable for functioning as a trans-tissue light collector. In this embodiment, the light collector 176 includes a light transmission portion 208 having an upper surface 210, an opposing generally planar collection surface 212, and peripheral side surfaces 214. Cladding 216 may cover the upper surface 210 and the peripheral surface 214 of the light transmission portion 208 so that only the collection surface 212 is exposed. Similarly to the previously discussed embodiments, a second cladding 219 may be disposed over the cladding 216 for protection, blocking ambient light from being received by the light detector 188, or both. In the embodiment shown in FIG. 11, it may be desirable to form the light transmission portion 208 from a conformable polymeric material that has suitable optical properties to facilitate contact between a substantial portion of the collection surface 212 and the tissue 198. Of course, the light transmission portion 208 and claddings 216 and 219 may be formed from the same materials as discussed above with respect to FIGS. 7A-7B.

According to some embodiments, the trans-tissue light collector 176 may be configured as a trans-dermal light collector wherein the tissue 198 includes an outside surface of the subject. According to other embodiments, the trans-tissue light collector 176 may be configured to reside on an internal body tissue in a cavity separate from the body cavity in which the scanning tip 128 is placed. For example, the scanning tip 128 may be inserted through a conventional trocar housing 209 and into a first body cavity such as, for example, within an internal space outside of an organ such as the stomach. The light collector 176 may be inserted into another body cavity such as by threading through the upper gastrointestinal (GI) tract and into the stomach. Light scanned by the scanning tip 128 against the outside of the stomach may thus be collected inside the stomach with the light collector 176 shown in FIG. 11.

When used as a trans-tissue light collector, a conventional trocar housing 209 may be inserted at an incision and the scanning tip 128 inserted therethrough. As performed in the embodiment of FIG. 11, the body cavity 200 may be sufflated, if desired. The scanning tip 128 scans the beam 204 across a FOV. Some of the light from the scanned beam 204 is reflected from the interior surface 202 of the body cavity 200 shown as reflected light 206, while some light from the scanned beam 204 is transmitted through wall 218 as transmitted light 220. At least some of the transmitted light 220 is received by the collection surface 212 of the light transmission portion 208. The transmitted light 220 received by the light transmission portion 208 propagates to the light detector 188. The intensity of the transmitted light 220 may be sensitive to density variations in the wall 218. The intensity of the transmitted light 220 may be lower in dense regions of the wall 218 and higher in less dense regions. As previously discussed, the electrical signals are further processed by the controller 102 to generate an image characteristic of the interior surface 202 of the cavity 200 that may be displayed on the monitor 104.

While the foregoing detailed description of the embodiments has referred to the use of cladding to reduce or eliminate ambient light exposure to light collectors that may be positioned to receive ambient light, it may not be necessary to reduce the amount of ambient light reaching the collection and/or detection region. In such embodiments, signals corresponding to the received light may be high-pass filtered to retrieve the portion of the signal likely to correspond to the rapidly scanning beam and eliminate spurious content associated with lower frequency sources. Lower frequency sources may include fluorescent sources that switch with frequencies in the 120 Hz range (and may have harmonics at higher frequencies) as well as substantially DC sources that may vary in the sub-Hz range, resulting from movement of objects between operating theater lighting and the light collector.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A scanned beam endoscope, comprising:
    a scanning tip operable to scan a beam across a field-of-view (FOV); and
    a light collector structured to collect scanned light affected by the FOV, the light collector being positionable relative to the scanning tip, wherein the light collector forms at least part of a trocar, the trocar including a housing having a bore therethrough dimensioned so that the scanning tip can be inserted through the bore.

2. The scanned beam endoscope of claim 1 wherein the light collector comprises a light detector operable to convert optical signals corresponding to the collected light to electrical signals.

3. The scanned beam endoscope of claim 1, further comprising a light detector coupled to the light collector to receive the collected light therefrom, the light detector operable to convert optical signals corresponding to the collected light to electrical signals.

4. The scanned beam endoscope of claim 2 or 3 wherein the light detector comprises at least one light detection element.

5. The scanned beam endoscope of claim 4 wherein the at least one light detection element comprises a photodiode.

6. The scanned beam endoscope of claim 2 or 3 wherein the light detector comprises a plurality of light detection elements.

7. The scanned beam endoscope of claim 6 wherein each of the detection elements comprises a photodiode.

8. The scanned beam endoscope of claim 1 wherein the light collector comprises:
    a light transmission portion formed of a material at least partially transparent to the affected light; and
    a first cladding portion covering a portion of the light transmission portion to define a light collection region on the light transmission portion.

9. The scanned beam endoscope of claim 8 wherein the first cladding portion has an index of refraction less than an index of refraction of the light transmission portion.

10. The scanned beam endoscope of claim 8 wherein the first cladding portion comprises a metallic layer.

11. The scanned beam endoscope of claim 8, further comprising a second cladding portion covering the first cladding portion.

12. The scanned beam endoscope of claim 8 wherein the material comprises a polymer.

13. The scanned beam endoscope of claim 8 wherein the material comprises a ceramic.

14. The scanned beam endoscope of claim 8 wherein the material comprises a glass.

15. The scanned beam endoscope of claim 1 wherein the light collector is formed of a material at least partially transparent to the affected light, the light collector having an outer surface covered by a cladding portion to define a light collection region on the light collector.

16. The scanned beam endoscope of claim 1 wherein the light collector has as a generally planar light collection surface.

17. The scanned beam endoscope of claim 16 wherein the light collector comprises:
a light transmission portion formed of a material at least partially transparent to the affected light; and
a cladding portion covering a portion of the light transmission portion and which does not cover the generally planar surface.

18. The scanned beam endoscope of claim 1 wherein the light collector comprises one or more optical fibers.

19. The scanned beam endoscope of claim 1 wherein the scanning tip comprises a MEMS scanner operable to scan the beam across the FOV.

20. The scanned beam endoscope of claim 1 wherein the scanning tip comprises a scanned beam source including a scanner operable to scan the beam out of an end of the scanning tip in a periodic pattern.

21. The scanned beam endoscope of claim 20 wherein the scanning tip comprises a scanned beam source including an illumination optical fiber positioned at least partially within the scanning tip, and wherein the scanner is positioned to receive light output from the illumination optical fiber and operable to scan the light as the beam across the FOV.

22. The scanned beam endoscope of claim 1 wherein the scanning tip comprises an optical fiber and an actuator, the actuator being operable to move the optical fiber in a periodic pattern to form a corresponding periodic light scanning pattern in the FOV.

23. The scanned beam endoscope of claim 1 wherein the light collector comprises a surgical tool.

24. The scanned beam endoscope of claim 1, further comprising a surgical tool attached to the light collector.

25. The scanned beam endoscope of claim 24 wherein the surgical tool comprises a scalpel.

26. The scanned beam endoscope of claim 24 wherein the surgical tool comprises a forceps.

27. The scanned beam endoscope of claim 1 wherein the light collector comprises a light transmission portion formed of a material at least partially transparent to the affected light and shaped to define a surgical tool.

28. The scanned beam endoscope of claim 1, further comprising a controller coupled to the light detector, the controller operable to process the electrical signals to generate an image characteristic of the FOV.

29. The scanned beam endoscope of claim 1, further comprising:
a controller coupled to the light detector, the controller operable to process the electrical signals; and
a display coupled to the controller and operable to show an image characteristic of the FOV.

30. A method of performing endoscopy, comprising:
introducing a scanning tip of an endoscope tip into a body cavity;
scanning a beam emitted from the scanning tip across a field-of-view (FOV) within the body cavity;
positioning a light collector relative to the scanning tip, wherein the act of positioning a light collector relative to the scanning tip comprises inserting the light collector through a working channel in the scanning tip; and
collecting at least a portion of light affected by the FOV with the light collector.

31. The method of claim 30 wherein:
the light collector forms at least part of a trocar including a housing having a bore therethrough; and
the act of positioning a light collector relative to the scanning tip comprises inserting at least a portion of the trocar through an incision made in a subject and into the body cavity.

32. The method of claim 31 wherein the act of introducing a scanning tip of an endoscope tip into a body cavity comprises inserting the scanning tip through the bore of the trocar.

33. The method of claim 30 wherein:
the act of positioning a light collector relative to the scanning tip comprises positioning the light collector proximate the exterior of the body cavity; and
the act of collecting at least a portion of light affected by the FOV with the light collector comprises transmitting the affected light through a wall of the body cavity.

34. The method of claim 30, further comprising displaying an image characteristic of the FOV.

35. The method of claim 30 wherein the affected light comprises light reflected from the FOV.

36. The method of claim 30:
wherein the scanning tip comprises at least another light collector; and
further comprising collecting at least a portion of the affected light with the at least another light collector.

37. The method of claim 36 wherein the act of collecting at least a portion of the affected light with the at least another light collector occurs prior to the act of collecting at least a portion of light affected by the FOV with the light collector.

* * * * *